US00PP09718P

United States Patent [19]

Fryer

[11] Patent Number: Plant 9,718

[45] Date of Patent: Dec. 3, 1996

[54] HYBRID TEA ROSE PLANT NAMED 'FRYXOTIC'

[75] Inventor: Gareth Fryer, Knutsford, England

[73] Assignee: Weeks Wholesale Rose Grower, Inc., Upland, Calif.

[21] Appl. No.: 564,798

[22] Filed: Nov. 29, 1995

[51] Int. Cl.[6] ..... A01H 5/00

[52] U.S. Cl. ..... Plt./11

[58] Field of Search ..... Plt./11, 16, 18

*Primary Examiner*—Howard J. Locker

*Attorney, Agent, or Firm*—Christie, Parker & Hale, LLP

[57] ABSTRACT

A new variety of Hybrid Tea rose suitable for garden decoration, having flowers of apricot pink coloration.

1 Drawing Sheet

BACKGROUND OF THE INVENTION

This invention relates to a new and distinct variety of Hybrid Tea rose. The varietal denomination of the new variety is 'Fryxotic'. It has as its seed parent the variety known as 'Pot O'Gold' and an unnamed undisseminated seedling as its pollen parent.

SUMMARY OF THE INVENTION

Among the features which distinguish the new variety from other presently available and known commercial rose cultivars are its unusual flower coloration of pink with an apricot gold center and its large full flowers and its reddened topside on the leaf rachis. 'Fryxotic' may be asexually propagated by cuttings, budding, or grafting.

Asexual reproduction of the new variety as performed in Kern County and Upland, Calif., by budding shows that the foregoing and other distinguishing characteristics come true to form and are established and transmitted through succeeding propagations.

COMPARISON WITH PARENTS

The new rose may be distinguished from its seed parent, 'Pot O'Gold' by the following combination of characteristics: whereas 'Fryxotic' bears flowers of a pink and apricot coloration, 'Pot O'Gold' bears flowers of a yellow coloration. Whereas the seed parent bears medium sized blooms in clusters, the new variety bears larger blooms mostly singly or in smaller clusters. The flowers of 'Pot O'Gold' are very fragrant, whereas the flowers of 'Fryxotic' have less pronounced fragrance.

The new variety may be distinguished from its pollen parent, an undisseminated seedling, by the following combination of characteristics: whereas the foliage of 'Fryxotic' is matte to semi-glossy, the foliage of the pollen parent is very glossy. The pollen parent bears flowers having about 30 petals and the new variety bears flowers of about 36 to 40 petals. The pollen parent bears many flowers in large clusters and 'Fryxotic' bears flowers mostly singly or in smaller clusters.

BRIEF DESCRIPTION OF THE ILLUSTRATION

The accompanying photograph illustrates the plant in color and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of September. Phenotypic expression may vary with environmental, cultural and climatic conditions, as well as differences in conditions of light and soil.

Flower

The new variety bears its flowers usually singly, sometimes in clusters of two to three blooms per stem. Flowers are borne in irregular, flat to rounded clusters on strong medium to long stems (about 16 to about 23 cm) Outdoors the plant blooms nearly continuolusly during the growing season and the flowers have a moderate fruity fragrance.

Bud

The peduncle is about 5.5 to about 7 cm and usually erect. It is almost entirely smooth with very few stipitate glands. Peduncle color is between 144B and 146B.

Before the calyx breaks, the bud is about 2 to about 2.5 cm in diameter at the widest point, medium to long in length, about 3 to about 3.5 cm in length, and pointed to ovoid in shaped with a moderately large receptacle. The surface of the bud bears some stipitate glands and many hairs, usually with slender foliaceous parts extending beyond the tip of the bud equal to about ¼ or more of its length. Bud color is between 144B and 146B.

The inner surface of the sepals is covered with fine wooly tomentum; sepal margins are lined with few stipitate glands and numerous hairs.

As the petals open, the bud is about 2.5 to about 3 cm in diameter at the widest point, about 3.5 to about 4 cm long, and moderately pointed to ovoid in form. The color of the upper and under surface of the newly opened petals is between 38D and 29D, deepening near the base to between 23C and 26C.

Bloom

When fully open, the bloom is about 11 to about 14 cm in diameter. Petalage is double with about 36 to 40 petals and about 3 to 7 petaloids arranged irregularly. When partially open, the bloom form is high centered and the petals are tightly spiraled with petal edges somewhat rolled outward. When fully open, the bloom form is more cupped to full and the petals are more loosely spiraled to undulated with petal edges moderately quilled outward.

Petals

The petals are of good substance and of medium thickness, with upper surfaces moderately satiny and under surfaces slightly shiny. The outer petals are nearly round to broadly obovate in shape with rounded apices. The inner petals are more narrowly obovate in shape with rounded apices.

Newly Opened Flower

The under and upper surface of the outer petals is between 38D and 29D, deepening at the base to between 24C and 26C. At the point where the petal attaches, there is a small zone of near 12B.

The under and upper surface of the intermediate and inner petals is beween 24C and 26D, deepening at the base to between 25B and 24A. At the point where the petal attaches, there is a small zone of near 12B.

The general tonality of the newly opened flower is between 38D and 29B, deepening toward the center of the flower to between 24C and 26D.

Three Day Old Flower

The under and upper surface of the outer and inner petals is between 36C and 29D with no deepening of color at the base. At the point where the petal attaches, there is a zone of near 12C.

The general tonality of the three day old flower is between 36C and 29D with no deepening of color toward the center of the flower.

On the spent bloom, the petals usually drop off cleanly.

In September, in Upland, Calif., blooms on the bush growing outdoors generally last from three to four or more days. Cut roses of plants grown outdoors kept at normal indoor living temperatures generally last from three to four or more days.

Male Reproductive Organs

Stamens are numerous and are arranged regularly about the pistil; a few are mixed with petaloids or tucked in the calyx. The filaments are very uneven in length, most with anthers. The anthers are medium size and all open approximately at the same. Anther color is near 17B when immature and near 167A at maturity. Pollen is moderate to abundant and near 16D in color.

Female Reproductive Organs

Pistils are average to many (approximately 110). The styles are somewhat uneven, short in length, average in caliper, and somewhat tightly bunched. Stigma color is near 4C. Style color is near 4C suffused toward the end with near 40C. Ovaries are usually all enclosed in the calyx.

Hips are about 2 to about 2.5 cm, very round to globular in form, and near 24B in color when ripe. The hip surface is very smooth with thick fleshy walls. Seeds number approximately 14 to 25 and are medium to large in size.

Foliage

The compound leaves are usually comprised of three to five, but sometimes seven, leaflets. The leaves are about 8.5 to about 12 cm in length and about 9 to about 10.5 cm in width at the widest point, moderately heavy in texture, and matte to semi-glossy in finish. The leaflets are about 3.6 to about 5.2 cm in length and about 2.3 to about 4 cm in width at the widest point, shaped moderately oval to ovoate with acute slightly mucronate apices and somewhat round to acute bases. Their margins are simply serrate.

The upper surface of the mature leaf is between 137A and 139A. The under surface of the mature leaf is between 191B and 139D, sometimes moderately suffused with near 183D. The upper and under surface of the young leaf is near 144A, often heavily suffused with between 187A and 183A.

The rachis is of average caliper and somewhat smooth to deeply grooved with some stipitate glands on the edges of the upper side. The edges are often moderately suffused with between 187A and 183A. The under side of the rachis is moderately rough with some hairs, stipitate glands and few moderately small prickles.

The stipules are of medium length with moderately wide somewhat short straight points that usually turn out at an angle of less than 45 degrees and recurve toward the stem.

The plant displays an above average degree of resistance to powdery mildew and rust as compared to other commercial varieties grown under comparable conditions in Upland, Calif.

Growth

The plant has a bushy upright medium height to tall habit (about 140 to about 170 cm in height and about 90 to about 120 cm spread at the widest point), with very full branching. It displays very vigorous growth and the canes are of heavy caliper.

The color of the major stems is near 152C. They bear few large prickles which are moderately long (about 1 cm). The large prickles are almost straight with a medium length narrowly oval base; prickle color is near 165A.

The color of the branches is between 137D and 146b. They bear several large prickles which are moderately long (about 1 cm). The large prickles are almost straight with a medium length narrowly oval shaped base; prickle color is near 161B. The branches bear few small prickles of similar shape and coloration.

The color of the new shoots is near 144A often lightly suffused with between 184B and 187B. They bear several large prickles which are moderately long (about 1 cm). The large prickles are almost straight with a medium length narrowly oval base; prickle color is between 184B and 187B. The shoots bear few small prickles of similar shape and coloration.

I claim:

1. A new and distinct variety of Hybrid Tea rose plant substantially as described and illustrated herein.

* * * * *

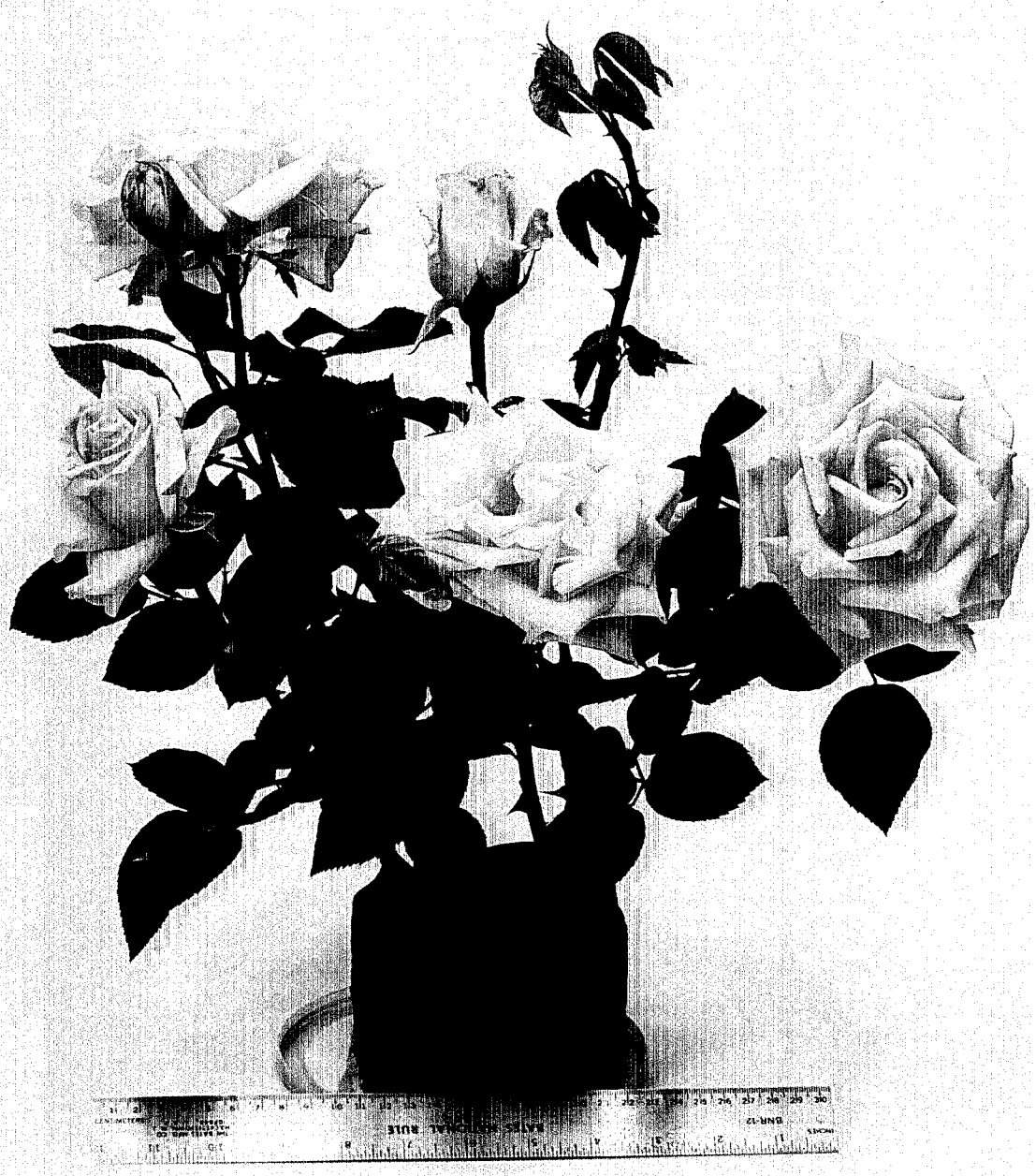

UNITED STATES PATENT AND TRADEMARK OFFICE

CERTIFICATE OF CORRECTION

PATENT NO. : Plant 9,718
DATED : December 3, 1996
INVENTOR(S) : Gareth Fryer

It is certified that error appears in the above-indentified patent and that said Letters Patent is hereby corrected as shown below:

Column 2, line 15, change "continuolusly" to -- continuously --.
Column 2, line 26, change "shaped" to -- shape --.
Column 4, line 9, change "ovoate" to -- ovate --.
Column 4, line 42, change "146b" to -- 146B --.

Signed and Sealed this

Second Day of December, 1997

*Attest:*

*Attesting Officer*

BRUCE LEHMAN

*Commissioner of Patents and Trademarks*